(12) United States Patent
Temko et al.

(10) Patent No.: US 10,667,761 B2
(45) Date of Patent: Jun. 2, 2020

(54) REAL TIME AUDIFICATION OF NEONATAL ELECTROENCEPHALOGRAM (EEG) SIGNALS

(71) Applicant: UNIVERSITY COLLEGE CORK—NATIONAL UNIVERSITY OF IRELAND, CORK, Cork (IE)

(72) Inventors: Andriy Temko, Cork (IE); Gordon Lightbody, Cork (IE); Liam Marnane, Cork (IE); Geraldine Boylan, Cork (IE)

(73) Assignee: University College Cork, Cork (IE)

( * ) Notice: Subject to any disclaimer, the term of this patent is extended or adjusted under 35 U.S.C. 154(b) by 648 days.

(21) Appl. No.: 15/324,401

(22) PCT Filed: Jul. 7, 2015

(86) PCT No.: PCT/EP2015/065515
§ 371 (c)(1),
(2) Date: Jan. 6, 2017

(87) PCT Pub. No.: WO2016/005403
PCT Pub. Date: Jan. 14, 2016

(65) Prior Publication Data
US 2017/0172523 A1 Jun. 22, 2017

Related U.S. Application Data

(60) Provisional application No. 62/021,457, filed on Jul. 7, 2014.

(30) Foreign Application Priority Data

Jul. 7, 2014 (GB) .................................. 1412071.1

(51) Int. Cl.
*A61B 5/0476* (2006.01)
*A61B 5/00* (2006.01)
(Continued)

(52) U.S. Cl.
CPC .......... *A61B 5/7415* (2013.01); *A61B 5/0476* (2013.01); *A61B 5/7405* (2013.01);
(Continued)

(58) Field of Classification Search
CPC ... A61B 5/7415; A61B 5/0476; A61B 5/7405; A61B 2503/045; G10L 19/16; H04S 5/00;
(Continued)

(56) References Cited

U.S. PATENT DOCUMENTS 7,222,054 B2 *  5/2007  Geva ..................... A61B 5/1112
                                                          340/539.12
9,888,884 B2 *  2/2018  Chafe .................. A61B 5/7415
(Continued)

FOREIGN PATENT DOCUMENTS

WO  WO-2010115939 A2 * 10/2010  ........... A61B 5/0476

OTHER PUBLICATIONS

Baier et al., "Event-based sonification of EEG rhythms in real time", Clin Neurophysiol. 118(6):1377-1386 (2007).
(Continued)

*Primary Examiner* — Navin Natnithithadha
(74) *Attorney, Agent, or Firm* — Nixon Peabody LLP; David S. Resnick; David F. Crosby (57) ABSTRACT

The present invention discloses a method and system of providing a real time audification of neonatal EEG signals. The method comprises the steps of: receiving preprocessed neonatal EEG signals; changing a characteristic of the preprocessed signals in a phase vocoder; resampling the output signals from the vocoder to a predetermined audio frequency range; converting the resampled signals into stereo signals; and selecting a plurality of channels from the stereo signals as the output audio signals.

13 Claims, 4 Drawing Sheets

(51) Int. Cl.
*G10L 19/16* (2013.01)
*H04S 5/00* (2006.01)

(52) U.S. Cl.
CPC .............. *G10L 19/16* (2013.01); *H04S 5/00* (2013.01); *A61B 2503/045* (2013.01); *G10H 2220/376* (2013.01); *G10H 2250/235* (2013.01); *G10H 2250/315* (2013.01); *H04S 2400/13* (2013.01)

(58) Field of Classification Search
CPC .......... H04S 2400/13; G10H 2220/376; G10H 2250/235; G10H 2250/315
USPC ................................................. 600/544, 545
See application file for complete search history.

(56) References Cited

U.S. PATENT DOCUMENTS

| | | | | |
|---|---|---|---|---|
| 10,136,862 | B2* | 11/2018 | Chafe | A61B 5/7415 |
| 10,321,842 | B2* | 6/2019 | Garten | A61B 5/04845 |
| 2012/0101401 | A1* | 4/2012 | Faul | A61B 5/0476 |
| | | | | 600/544 |
| 2015/0150520 | A1* | 6/2015 | Chafe | A61B 5/7415 |
| | | | | 600/483 |
| 2015/0297109 | A1* | 10/2015 | Garten | A61B 5/04845 |
| | | | | 600/544 |

OTHER PUBLICATIONS

Hinterberger et al., "A multimodal brain-based feedback and communication system", Exp Brain Res. 154(4):521-526 (2004).
Kaniwa et al., "EEG steady state synchrony patterns sonification", Signal & Information Processing Association Annual Summit and Conference (APSIPA ASC), 2012 Asia-Pacific, IEEE 6 pp. (2012).
Olivan et al., "Easy listening to sleep recordings: tools and examples", Sleep Med. 5(6):601-603 (2004).
Temko et al., "EEG 'diarization'For the description of neonatal brain injuries", 2014 IEEE International Conference on Acoustics, Speech and Signal Processing (ICASSP). IEEE, 6pp. (2014).
Temko et al., "EEG signal description with spectral-envelope-based speech recognition features for detection of neonatal seizures", IEEE Trans Inf Technol Biomed. 15(6):839-847 (2011).
Thomas et al., "Gaussian mixture models for classification of neonatal seizures using EEG", Physiol Meas. 31(7):1047-1064 (2010).

* cited by examiner

REAL TIME AUDIFICATION OF NEONATAL ELECTROENCEPHALOGRAM (EEG) SIGNALS

CROSS REFERENCE TO RELATED APPLICATIONS

This application is a 35 U.S.C. § 371 National Phase Entry Application of International Application No. PCT/EP2015/065515, filed on Jul. 7, 2015, which designates the U.S. and which claims priority to GB Application No. 1412071.1 filed on Jul. 7, 2014 and U.S. Provisional Application No. 62/021,457 filed on Jul. 7, 2014, the contents of each of which are incorporated herein by reference in their entirety.

FIELD

The present invention is concerned with neonatal electroencephalogram (EEG) signals.

BACKGROUND

Neonatal seizures are the most common neurological emergency in the neonate and are a serious concern for clinicians and parents worldwide. Only about one third of all neonatal seizures are clinically visible and many remain undetected in the busy Neonatal Intensive Care Unit (NICU) environment. The only method available to detect all neonatal seizures accurately is continuous multi-channel EEG monitoring. Interpretation of neonatal EEG requires a neurophysiologist or paediatric neurologist with specific expertise in neonatal EEG. This expertise is not available on a 24 h basis, 7 days a week. To fill the gap in the availability of appropriate expertise, clinical staff in the NICU often use a simpler form of EEG monitoring, known as amplitude integrated EEG (aEEG). Amplitude integrated EEG is an logarithmically-scaled, temporally-smoothed and compressed display of EEG which is usually computed from two EEG channels, one from each hemisphere. Despite the fact that many short and focal neonatal seizures are undetectable with aEEG and inter-observer agreement is poor, aEEG currently serves as a trade-off between very inaccurate clinical detection of seizures and very accurate but scarcely available neurophysiologic expertise, and thus is widely adopted worldwide in the NICU.

In view of the above mentioned problems associated with the use of aEEG, it will be appreciated that an automated decision support system that could detect and annotate seizures on the neonatal EEG would be extremely useful for clinicians in the NICU.

In this regard, it is believed that human hearing input is better than the visual input when it comes to assessing both the spatial and temporal evolution of the frequency characteristics of a signal. Hearing is flexible and low-cost. Hearing also allows for faster processing than visual presentation, has better temporal resolution, and represents an additional information channel, releasing visual sense for other tasks. Therefore, an automated decision support system that could detect and annotate seizures on the neonatal EEG through the use of audio would be desirable.

It is known to audify the EEG signals of adults, for purposes such as to detect epilepsy. One such audification method involves lifting an adult's recorded brain frequencies into the human audible range, by saving the original waveform with a higher sampling rate. In this signal resampling process, time and pitch manipulations are always linked so that time compression scales pitches upwards, time stretching scales pitches downwards. However, with this direct EEG audification, the resultant audio sounds noisy. Furthermore, real-time EEG playback is also not possible.

Another such audification method of adult EEG signals is to map EEG spectral frequencies to the audible range by sonification. In this process, the dominant EEG frequencies are extracted using the fast Fourier transform, and then the tones of the mapped frequencies are created with pre-specified parameters such as duration and pitch. However, it should be appreciated that when sonification is used, what is heard by a listener is not the real EEG, but rather 'synthetic' artificially generated audio waveforms which have been extracted from the original EEG content.

Accordingly, an object of the present invention is to provide a method and system for the audification of neonatal EEG signals which overcomes at least one of above mentioned problems associated with existing adult EEG signal audification methods.

SUMMARY

The present invention provides a method of providing a real time audification of neonatal EEG signals, comprising the steps of:
  receiving preprocessed neonatal EEG signals;
  changing a characteristic of the preprocessed signals in a phase vocoder;
  resampling the output signals from the phase vocoder to a predetermined audio frequency range;
  converting the resampled signals into stereo signals; and
  selecting a plurality of channels from the stereo signals to form an output audio signal.

This method provides an audification of a neonate's EEG signals which time stretches without affecting the pitch, and pitch scales without affecting the signal duration. In addition, the method enables direct EEG playback without any artificially created synthetic sounds.

The step of converting the resampled signals into stereo signals may comprise the step of converting the resampled signals into left and right stereo channels corresponding to left and right brain hemispheres.

The step of selecting a plurality of channels from the stereo signals to form the output audio signal may comprise the step of selecting a channel from the left stereo channel and selecting a channel from the right stereo channel to form the output audio signal.

The method may further comprise the steps of:
  determining segments of the output audio signal which satisfy a predetermined criterion; and
  amplifying the gain of the output audio signal for the determined segments.

The step of selecting a channel from the left stereo channel and selecting a channel from the right stereo channel as the output audio signal may further comprise the steps of:
  determining a channel from the left brain hemisphere and a channel from the right brain hemisphere which has the highest cumulative probability of exhibiting a seizure; and
  selecting the determined channel from the left brain hemisphere and the determined channel from the right brain hemisphere to form the output audio signal.

The step of determining segments of the output audio signal which satisfy a predetermined criterion may correspond to determining those segments which have the highest probability of exhibiting a seizure.

Preferably, the temporal characteristics of the preprocessed signals are changed.

The changing of the temporal characteristics of the preprocessed signals may comprise the steps of:
segmenting the preprocessed signal into overlapping frames;
applying the short-time Fourier transform to each frame;
separating the magnitude and phase of each frame;
estimating the instantaneous frequency of each frame;
determining the phase function associated with the frames; and
performing the inverse short-time Fourier transform on each frame.

The temporal characteristic of the signal spectrogram may be changed by slowing down the preprocessed signals by a factor of 100.

The resampling may correspond to mapping those frequencies known to correspond to the dominant frequencies of a seizure to the audible frequency range.

The predetermined audio frequency range may correspond to 3-4 KHz.

The step of preprocessing the neonatal EEG signals may correspond to:
filtering of the EEG signals by low pass and high pass filters; and
downsampling the frequency of the signals to 32 Hz.

The downsampling may correspond to 32 Hz.

The output signals from the vocoder may be resampled at a 32 kHz sampling rate.

The present invention also provides a system for providing a real time audification of neonatal EEG signals, comprising:
means or module for receiving preprocessed neonatal EEG signals;
means or module for changing a characteristic of the preprocessed signals in a phase vocoder;
means or module for resampling the output signals from the vocoder to a predetermined audio frequency range;
means or module for converting the resampled signals into stereo signals; and
means or module for selecting a plurality of channels from the stereo signals as the output audio signals.

In another embodiment there is provided a method of providing a real time audification of neonatal EEG signals, comprising the steps of:
receiving preprocessed neonatal EEG signals;
changing a characteristic of the preprocessed signals in a phase vocoder with application specific parameters in order to increase audio intelligibility of the neonatal EEG signals;
re-sampling the output signals from the phase vocoder to a predetermined audio frequency range to match a human hearing system;
converting the re-sampled signals into stereo audio signals and playing the created stereo audio; and
selecting a plurality of channels from the signals to form an output stereo audio signal.

There is also provided a computer program comprising program instructions for causing a computer program to carry out the above method which may be embodied on a record medium, carrier signal or read-only memory.

BRIEF DESCRIPTION OF THE DRAWINGS

The invention will be more clearly understood from the following description of an embodiment thereof, given by way of example only, with reference to the accompanying drawings, in which.

DETAILED DESCRIPTION OF THE DRAWINGS

The present invention provides a method and system for listening to the EEG of newborn babies or neonates. By listening to the EEG of a neonate, various patterns of the EEG signals can be detected by the listener. In the described embodiment of the invention, such patterns are used to indicate to the listener the presence of a seizure in the brain of a neonate.

Figure 1:
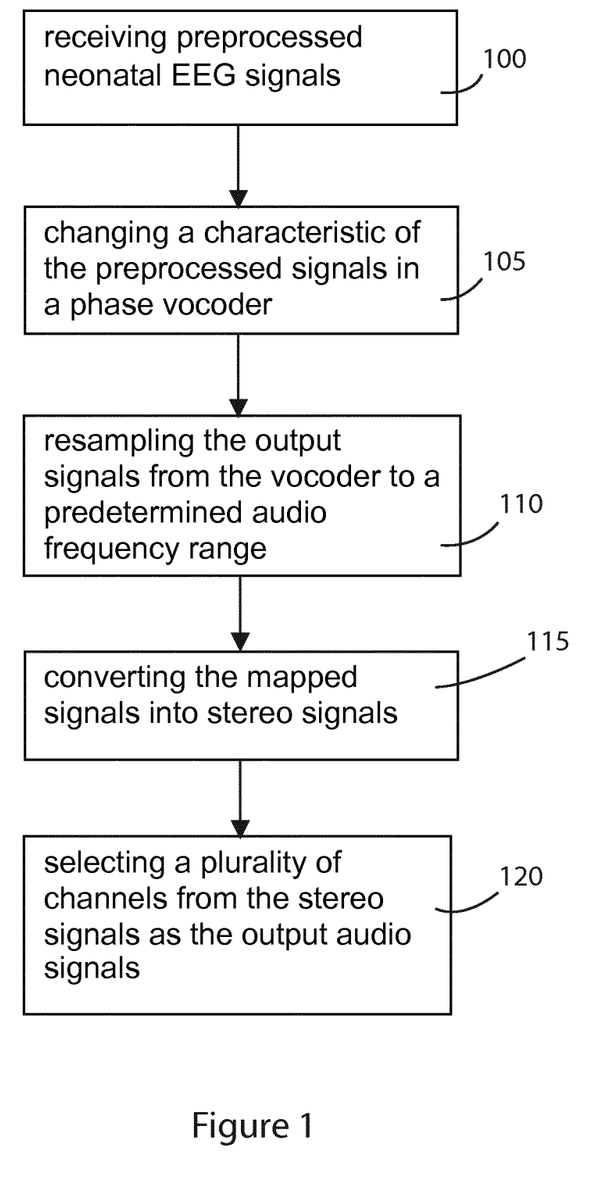
FIG. 1 details the main steps in the process of the invention which provides a real time audification of neonatal EEG signals.

FIG. 1 details the main steps in the process of the invention which provides a real time audification of neonatal EEG signals. In step 100 preprocessed neonatal EEG signals are received. In step 105, a characteristic of the preprocessed signals is changed in a phase vocoder. The output signals from the vocoder are then resampled to a predetermined audio frequency range (step 110). The resampled signals are then converted into stereo signals (step 115). Finally, a plurality of channels from the stereo signals are selected as the output audio signals (step 120).

Figure 2:
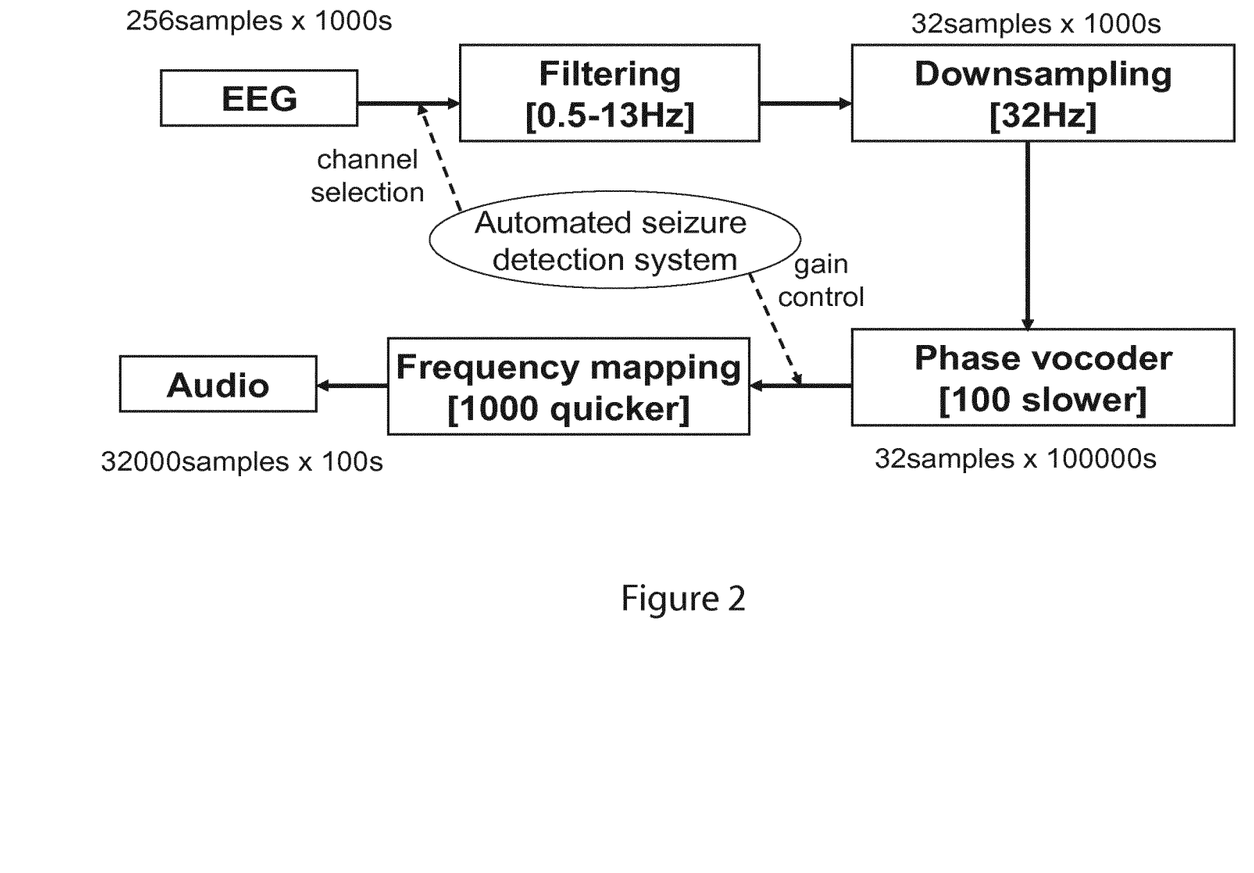
FIG. 2 shows a flowchart for the audification of neonatal EEGs.

FIG. 2 details the main steps in one embodiment of the audification process of the present invention, with an example of 1000s of EEG as an input. In the first step, the output signals of the EEG are pre-processed prior to being input to a vocoder through the filtering of the EEG signals by low pass and high pass filters, to attenuate any unwanted information. This is followed by the downsampling of the frequency of the signals to 32 Hz.

In the vocoder, the temporal characteristics of the signals are changed. This intuitively corresponds to stretching the time-base of the signal spectrogram while retaining their short-time spectral characteristics. Therefore, the signals are slowed down by a factor of N, which in the preferred embodiment has a value of 100. These signals are then resampled to an audible range.

In the frequency mapper, the output signals from the vocoder are resampled at a 32 kHz sampling rate. This corresponds to pitch shifting the original frequency range of 0.5-16 Hz to a new range of 0.5-16 kHz. Through frequency mapping, the most dominant frequencies of seizure (typically 0.5-6 kHz) can be mapped to signals within the audible range, in particular to the range of human scream, namely 3-4 kHz.

As a result, the EEG real-time playback is sped up by a factor which is inversely proportional to N. It will be appreciated that this provides for a significant time saving for the listener, for example where in the preferred embodiment 1 hour of EEG can be played back in around 6 minutes.

In a further step, the audio signals are converted into stereo signals, such that the left stereo signal corresponds to the left brain hemisphere and the right stereo signal corresponds to the right brain hemisphere. These stereo signals are then input to a seizure detection module. The output of the seizure detection module corresponds to the final audified EEG signal.

Figure 3:
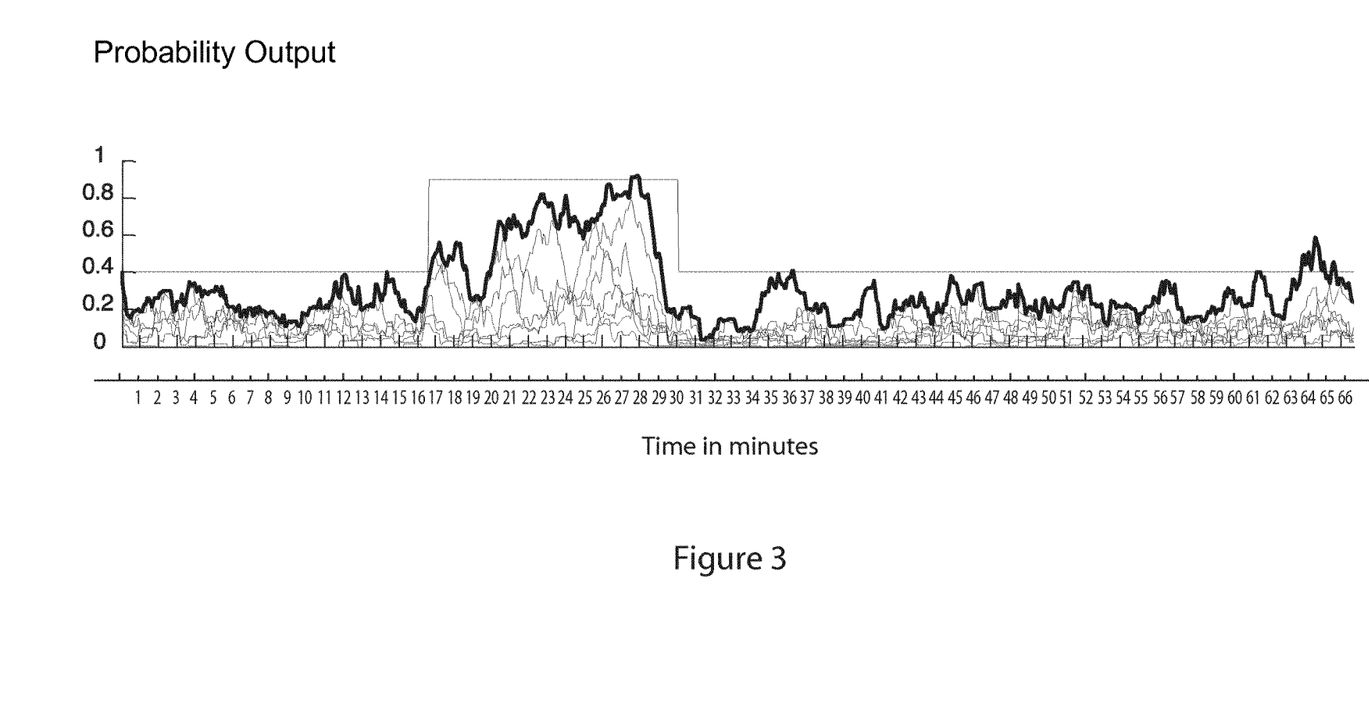
FIG. 3 shows a probabilistic output for each stereo channel representing the EEG signal.

In the preferred embodiment of the seizure detection module, the channel from each hemisphere which is determined to have the highest cumulative probability of a seizure event is selected to form the output audio signal. This is determined by computing the cumulative seizure probability from the per-channel probabilistic outputs which are shown in FIG. 3, which shows a plot of probability output for each channel versus time (in minutes). The channels with the maximum cumulative probability is taken separately from the left (F3-C3, C3-O1, Cz-C3, C3-T3) and right hemisphere (F4-C4, C4-O2, T4-C4, C4-Cz). In this figure, the maximum probabilistic output across channel is shown in bold, while seizure onset and offset are annotated as 16m37s-30m05s and superimposed on top in red. The signal gain is also controlled by the probabilistic output of the system, such that the signal is multiplied by the maximum probabilistic output of the system. As a result, EEG segments which are likely to be seizures are more audible than the background.

Figure 4:
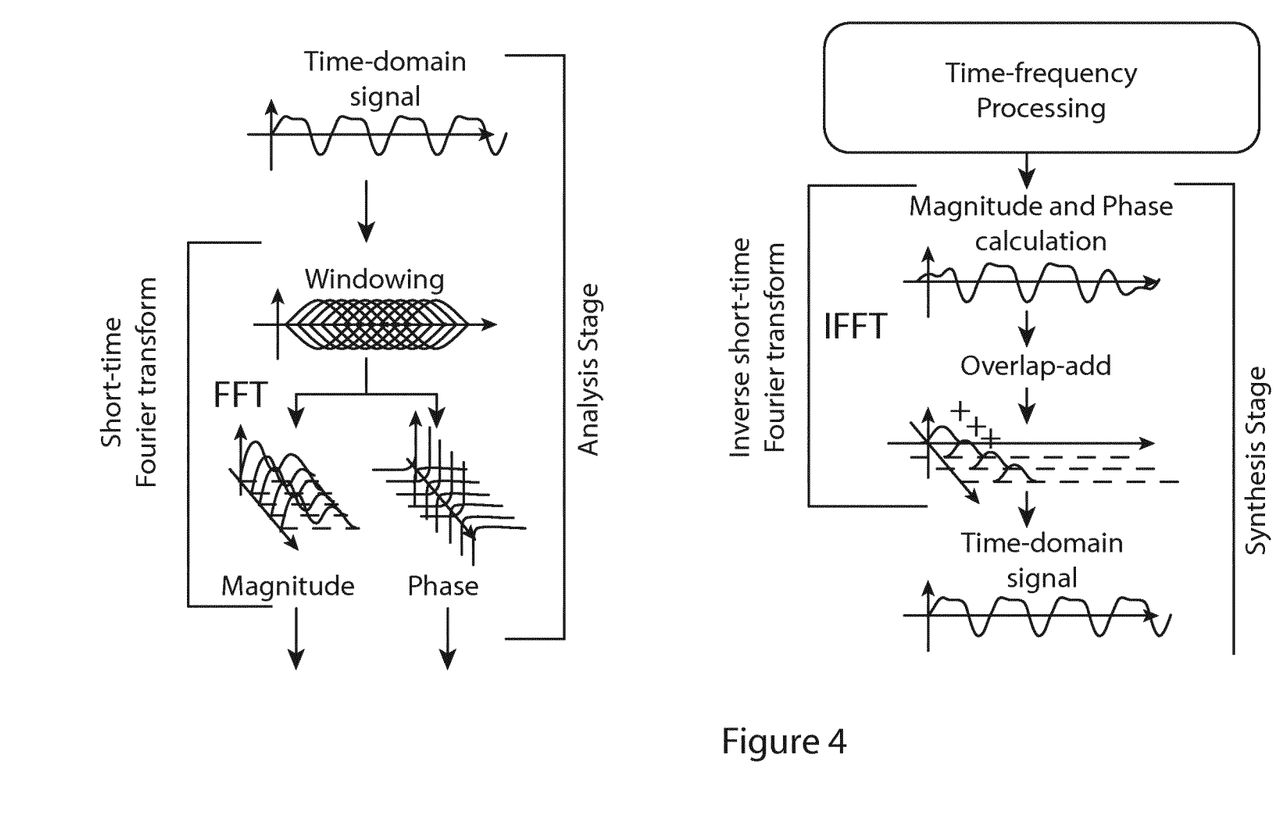
FIG. 4 shows a flowchart of the main processing steps of the phase vocoder of the present invention.

FIG. 4 shows a flowchart of the main processing steps of the phase vocoder of the present invention. It comprises three main processing stages, namely analysis, processing, and synthesis. During the analysis stage, the signal is segmented into overlapping frames with analysis time-instants $t_a = uR_a$, for an integer u, and the short-time Fourier transform (STFT) is then applied to each frame:

$$X(t_a^u, \Omega_k) = \sum_{n=-\infty}^{\infty} h(n) x(t_a^u + n) e^{-j\Omega_k n}$$

Where x is the original signal, h(n) is the analysis window, $\Omega_k = 2\pi k/N$ is the centre frequency of kth STFT channel, and N is the size of the STFT. $X(t,\Omega)$ is a function of both time and frequency.

In the synthesis stage, the inverse short-time Fourier transform is performed on each frame spectrum. The overlapping spectrum frames result in the output segments overlapping each other. The overlapping output segments are all summed together, yielding the following output signal (known as the overlap-add method) in the time domain:

$$y(n) = \frac{1}{N} \sum_{k=0}^{N-1} Y(t_s^u, \Omega_k) e^{j\Omega_k n}$$

In the absence of modifications, $t_s = \alpha t_a$, $\alpha = R_a/R_s = 1$, and the output signal is identical to the original signal, where $R_a$ and $R_s$ are the hop size of the analysis and synthesis, respectively. It should be noted that all modifications that are done in the spectrum representation need to preserve the appropriate correlation between adjacent frequency bins and time frames.

In the processing stage, the magnitude and phase are separated. The time evolution of sine-wave amplitude is modified simply by setting:

$$|Y(t_s^u, \Omega_k)| = |X(t_a^u, \Omega_k)|$$

In the synthesis stage, the process requires phase unwrapping. The phase, which is measured modulo $2\pi$, is unwraped by keeping track of cumulative phase variation and taking its principal determination between $\pm\pi$:

$$\Delta\Phi_k^u = \angle X(t_a^u, \Omega_k) - \angle X(t_a^{u-1}, \Omega_k) - R_a \Omega_k$$

Where $\angle X(t^u)$ and $\angle X(t^{u-1})$ are the phases at time instances $t^u$ and $t^{u-1}$, respectively. Phase unwrapping is a process whereby the phase increment between two consecutive frames is used to estimate the instantaneous frequency of the closest sinusoid:

$$w_k(t_a^u) = \Omega_k + \frac{1}{R_a} \Delta\phi_k^u$$

where $w_k$ is the instantaneous frequency.

The phase increment $\Delta\Phi$ is simply the small phase shift resulting from $w_k$ being close but not equal to $\Phi_k$. Once the instantaneous frequency is estimated, the phase of the time-scaled output signal Y is set according to the phase-propagation formula $$\angle Y(t_s^u, \Omega_k) = \angle Y(t_s^{u-1}, \Omega_k) + R_s w_k(t_a^u)$$

This phase function can be decimated or interpolated to the new time scale, so that the phase of the output short-time Fourier Transform, STFT can be computed at any given synthesis time-instant:

$$\angle Y(t_s^u, \Omega_k) = \angle Y(t_s^0, \Omega_k) + \sum_{i=1}^{u} R_s w_k(t_a^i)$$

It will be appreciated that the method of audification of neonatal EEG signals of the present invention provides a number of advantages when compared to existing adult EEG signal audification methods. Firstly, the phase vocoder of the present invention allows for time stretching without affecting the pitch, and pitch scaling without affecting the signal duration. In addition, the method of the present invention enables direct EEG playback without any artificially created synthetic sounds.

While the present invention has been described in an application where the audification of a neonate's EEG signals are used as a unique audio alarm for seizures, the audification of present invention could equally be used in a number of other applications. For example, the audio signals could be used to help classify the different background EEG patterns occurring in term and preterm babies, and in the sleep state analysis of newborns. In addition, the audio signals could allow parents to 'listen' to their babies brain waves, and could also be played to sick newborns to help reduce stress.

The embodiments in the invention described with reference to the drawings comprise a computer apparatus and/or processes performed in a computer apparatus. However, the invention also extends to computer programs, particularly computer programs stored on or in a carrier adapted to bring the invention into practice. In particular computer programs for controlling the system and method as hereinbefore described. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

Additionally, at least a portion of the systems, methodologies and techniques described with respect to the exemplary embodiments of present disclosure can incorporate a machine, such as, but not limited to, computer system, or any other computing device within which a set of instructions, when executed, may cause the machine to perform any one or more of the methodologies or functions discussed above. The machine may be configured to facilitate various operations conducted by the systems disclosed herein. For example, the machine may be configured to, but is not limited to, assist the systems by providing processing power to assist with processing loads experienced in the systems, by providing storage capacity for storing instructions or data traversing the systems, or by assisting with any other operations conducted by or within the systems.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A method of providing a real time audification of neonatal EEG signals, comprising the steps of:
    receiving preprocessed neonatal EEG signals;
    changing a characteristic of the preprocessed neonatal signals in a phase vocoder;
    resampling output signals from the phase vocoder to a predetermined audio frequency range;
    converting the resampled signals into stereo signals;
    selecting a plurality of channels from the stereo signals to form an output stereo audio signal, and
    wherein the preprocessed neonatal signals include temporal characteristics and the method includes changing the temporal characteristics of the preprocessed neonatal signals by:
    segmenting the preprocessed neonatal signals into overlapping frames;
    applying a short-time Fourier transform to each frame;
    separating a magnitude and phase of each frame;
    estimating an instantaneous frequency of each frame;
    determining a phase function associated with the frames; and
    performing an inverse short-time Fourier transform on each frame.

2. The method of claim 1, wherein the step of converting the resampled signals into stereo signals comprises the step of converting the resampled signals into left and right stereo channels corresponding to left and right brain hemispheres.

3. The method of claim 1, wherein the step of selecting a plurality of channels from the stereo signals to form the output audio signal comprises the step of selecting a channel from a left stereo channel and selecting a channel from a right stereo channel to form the output audio signal.

4. The method of claim 3, further comprising the step of:
    determining segments of the output audio signal which satisfy a predetermined criterion; and
    amplifying the gain of the output audio signal for the determined segments.

5. The method of claim 3, wherein the step of selecting a channel from the left stereo channel and selecting a channel from the right stereo channel as the output audio signal further comprises the steps of:
    determining a channel from the left brain hemisphere and a channel from the right brain hemisphere which has the highest cumulative probability of exhibiting a seizure; and
    selecting the determined channel from the left brain hemisphere and the determined channel from the right brain hemisphere to form the output audio signal.

6. The method of claim 3, comprising the step of determining segments of the output audio signal which satisfy a predetermined criterion corresponds to determining those segments which have the highest probability of exhibiting a seizure.

7. The method of claim 1, wherein a temporal characteristic of the preprocessed neonatal EEG signals is changed by slowing down the preprocessed neonatal EEG signals by a factor of 100.

8. The method of claim 1 wherein the resampling corresponds to mapping those frequencies known to correspond to the dominant frequencies of a seizure to the audible frequency range.

9. The method of claim 1, wherein the predetermined audio frequency range corresponds to 3-4 KHz.

10. The method of claim 1, further comprising the steps of preprocessing the neonatal EEG signals to produce preprocessed neonatal signals by:
    filtering of the neonatal EEG signals by low pass and high pass filters; and
    downsampling the frequency of the filtered neonatal EEG signals to 32 Hz.

11. The method of claim 1, wherein the output signals from the vocoder are resampled at a 32 kHz sampling rate.

12. A system for providing a real time audification of neonatal EEG signals, comprising:
    means for receiving preprocessed neonatal EEG signals;
    means for changing a characteristic of the preprocessed signals in a phase vocoder;
    means for resampling output signals from the vocoder to a predetermined audio frequency range;
    means for converting the resampled signals into stereo signals; and
    means for selecting a plurality of channels from the stereo signals as the output audio signals, and
    wherein the preprocessed neonatal signals include temporal characteristics and the system further includes means for changing the temporal characteristics of the preprocessed neonatal signal comprising:
    means for segmenting the preprocessed neonatal signals into overlapping frames;
    means for applying a short-time Fourier transform to each frame;

means for separating a magnitude and phase of each frame;

means for estimating an instantaneous frequency of each frame;

means for determining a phase function associated with the frames; and means for performing an inverse short-time Fourier transform on each frame.

13. A method of providing a real time audification of neonatal EEG signals, comprising the steps of:

receiving preprocessed neonatal EEG signals;

changing a characteristic of the preprocessed signals in a phase vocoder with application specific parameters in order to increase audio intelligibility of the neonatal EEG signals;

re-sampling output signals from the phase vocoder to a predetermined audio frequency range to match a human hearing system;

converting the re-sampled signals into stereo audio signals and playing the created stereo audio; and selecting a plurality of channels from the signals to form an output stereo audio signal, and wherein the preprocessed neonatal signals include temporal characteristics and the method includes changing the temporal characteristics of the preprocessed neonatal signal by:

segmenting the preprocessed neonatal signals into overlapping frames;

applying a short-time Fourier transform to each frame;

separating a magnitude and phase of each frame;

estimating an instantaneous frequency of each frame;

determining a phase function associated with the frames; and performing an inverse short-time Fourier transform on each frame.

* * * * *